(12) United States Patent
Krizman et al.

(10) Patent No.: US 10,203,336 B2
(45) Date of Patent: Feb. 12, 2019

(54) SRM/MRM ASSAY FOR THE TYROSINE-PROTEIN KINASE RECEPTOR UFO (AXL) PROTEIN

(71) Applicant: Expression Pathology, Inc., Rockville, MD (US)

(72) Inventors: David B. Krizman, Gaithersburg, MD (US); Todd Hembrough, Gaithersburg, MD (US); Adele Blackler, Rockville, MD (US); Wei-Li Liao, Herndon, VA (US)

(73) Assignee: Expression Pathology, Inc., Rockville, MD (US)

( * ) Notice: Subject to any disclaimer, the term of this patent is extended or adjusted under 35 U.S.C. 154(b) by 17 days.

(21) Appl. No.: 15/307,753

(22) PCT Filed: Apr. 30, 2015

(86) PCT No.: PCT/US2015/028667
§ 371 (c)(1),
(2) Date: Oct. 28, 2016

(87) PCT Pub. No.: WO2015/168484
PCT Pub. Date: Nov. 5, 2015

(65) Prior Publication Data
US 2017/0052196 A1    Feb. 23, 2017

Related U.S. Application Data

(60) Provisional application No. 61/986,688, filed on Apr. 30, 2014.

(51) Int. Cl.
*G01N 33/68* (2006.01)
*G01N 33/574* (2006.01)

(52) U.S. Cl.
CPC ... *G01N 33/6848* (2013.01); *G01N 33/57492* (2013.01); *G01N 33/68* (2013.01); *G01N 2333/912* (2013.01); *G01N 2333/91205* (2013.01); *G01N 2800/56* (2013.01); *G01N 2800/7028* (2013.01)

(58) Field of Classification Search
CPC ... G01N 2333/912; G01N 2333/91205; G01N 2800/56; G01N 2800/7028; G01N 33/68; G01N 33/6848; G01N 33/57492
See application file for complete search history.

(56) References Cited

U.S. PATENT DOCUMENTS

| 7,473,532 | B2 | 1/2009 | Darfler et al. |
| 2009/0253156 | A1 | 10/2009 | Patton et al. |
| 2011/0105732 | A1 | 5/2011 | Guo et al. |
| 2011/0275065 | A1 | 11/2011 | Walfish et al. |

FOREIGN PATENT DOCUMENTS

| WO | WO2007140352 | * 12/2007 | ........... C12Q 1/6886 |
| WO | 2010103388 A2 | 9/2010 | |
| WO | 2011053779 A2 | 5/2011 | |
| WO | 2013055780 A1 | 4/2013 | |

OTHER PUBLICATIONS

Wiśniewski, J.R. Proteomic Sample Preparation from Formalin Fixed and Paraffin Embedded Tissue. J. Vis. Exp., 2013. vol. 79, e50589, pp. 1-5. (Year: 2013).*
Thompson et al. Impact of pre-analytical factors on the proteomic analysis of formalin-fixed paraffin-embedded tissue. Proteomics Clin. Appl. 2013, 7, 241-251. First published Oct. 2, 2012 (Year: 2012).*
Boja et al Mass spectrometry-based targeted quantitative proteomics: Achieving sensitive and reproducible detection of proteins. Proteomics, 2012. vol. 12, pp. 1093-1110. (Year: 2012).*
Wisniewski. Protein Sample Preparation from Formalin Fixed and Paraffin Embedded Tissue. Journal of Visualized Experiments, Sep. 2, 2013. 5 pages. (Year: 2013).*
Ekman et al., Journal of Thrombosis and Haemostasis, 8: 838-844 (2010).
Ekman et al., Journal of Thrombosis and Haemostasis, 8: 838-844 (2010), supplementary information.
Liu et al., American Association for Cancer Research, 69: 6871-6878 (2009).
Liu et al., American Association for Cancer Research, 69: 6871-6878 (2009), supplementary information Figure 4.
Chaker et al., Proteomics, 13: 771-787 (2013).
Bai et al., Cancer Research, 72: 2501-2511 (2012).
Office Action in corresponding Australian Application No. 2015252961, dated Jun. 27, 2017 (9 pages).
Hill et al., Proteomics, 9: 535-549 (2009).
Wu et al., Molecular & Cellular Proteomics, 11: 1-14 (2012).
Leconet et al., Oncogene, 33: 5405-5414 (2014).
Lee et al., Annals of Surgical Oncology, 19: 500-508 (2011).
Gustafsson et al., Clinical Cancer Research, 15: 4742-4749 (2009).
Ou et al., Oncogene, 30: 1643-1652 (2011).
Extended European Search Report in corresponding European Application No. 15786066.9, dated Oct. 16, 2017 (10 pages).
International Search Report in Application No. PCT/US2015/28667, dated Jul. 31, 2015, 4 pages.

* cited by examiner

*Primary Examiner* — Marcela M Cordero Garcia
(74) *Attorney, Agent, or Firm* — Edell, Shapiro & Finnan, LLC

(57) ABSTRACT

Peptides from the tyrosine-protein kinase receptor UFO protein (AXL) are provided that are particularly advantageous for quantifying the AXL protein directly in biological samples that have been fixed in formalin by the method of Selected Reaction Monitoring (SRM)/Multiple Reaction Monitoring (MRM) mass spectrometry. Such biological samples are chemically preserved and fixed and include formalin-fixed tissue/cells, formalin-fixed/paraffin embedded (FFPE) tissue/cells, FFPE tissue blocks and cells from those blocks. A protein digest is prepared from the biological sample and the AXL protein is quantitated in the Liquid Tissue sample by the method of SRM/MRM mass spectrometry by quantitating in the protein sample at least one or more of the peptides described.

19 Claims, 1 Drawing Sheet
Specification includes a Sequence Listing.

A) Characteristics that define the SRM/MRM signature chromatographic peak of this peptide in a Liquid Tissue lysate from a formalin fixed biological sample

| SEQ ID | Peptide Sequence | Mono Isotopic Mass | Precursor Charge State | Precursor m/z | Transition m/z | Ion Type |
|---|---|---|---|---|---|---|
| SEQ ID NO: 4 | APLQGTLLGYR | 1188.3926 | 2 | 594.84 | 559.322 | Y10 |
| | | | 2 | 594.84 | 779.441 | Y7 |
| | | | 2 | 594.84 | 907.499 | Y8 |
| | | | 2 | 594.84 | 1020.583 | Y9 |

B) Demonstration of SRM/MRM signature precursor chromatographic peak for this peptide in a positive control sample and a Liquid Tissue lysate from a formalin fixed biological sample

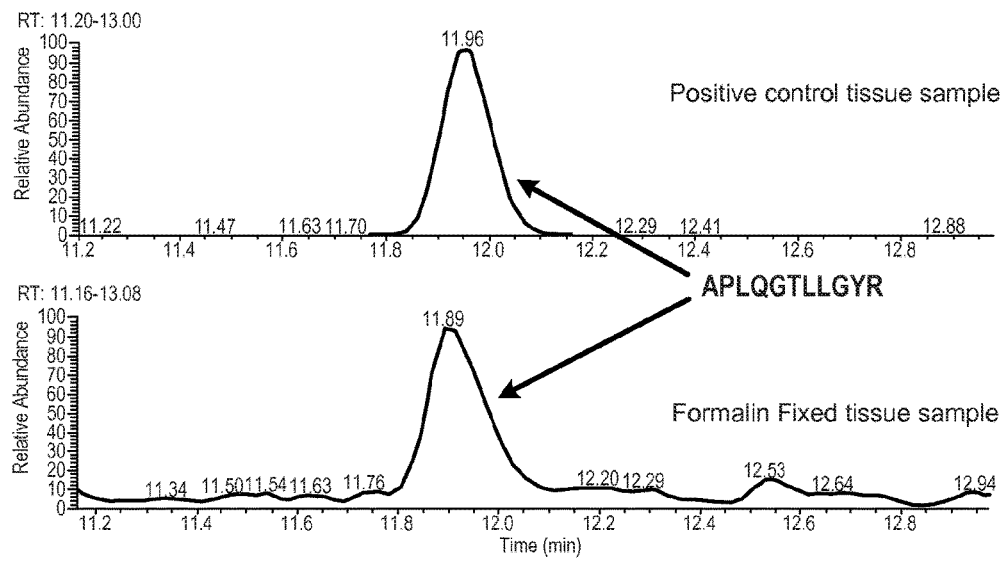

C) Four (4) characteristic transition ions that define the SRM/MRM signature of this peptide in Liquid Tissue lysates from formalin fixed biological samples

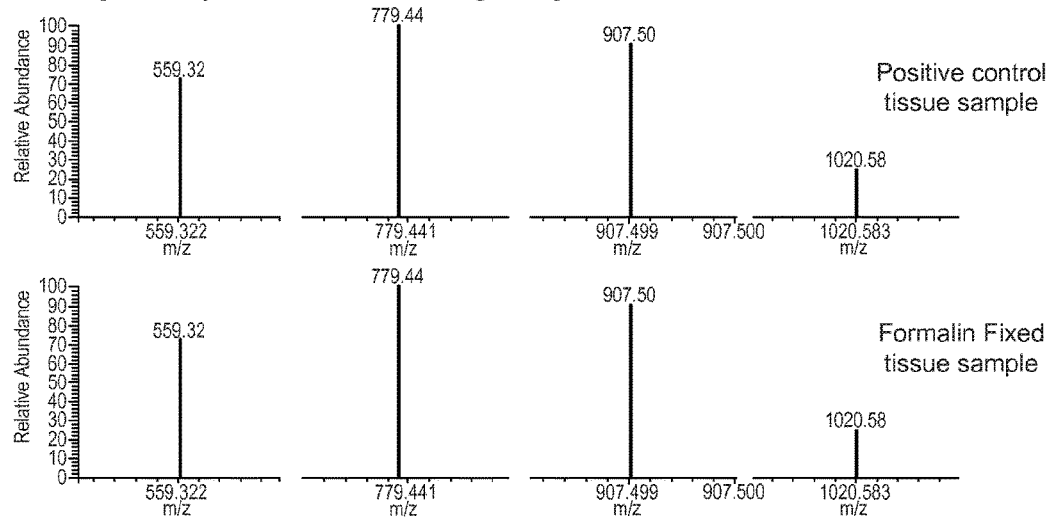

SRM/MRM ASSAY FOR THE TYROSINE-PROTEIN KINASE RECEPTOR UFO (AXL) PROTEIN

Cancer is treated with a collection of therapeutic agents that kill growing and dividing cells and that function in a variety of ways. A common collection of chemotherapeutic agents has been used for decades, either individually or in combinations, and this common collection of agents has become the traditional and routine cancer treatment in clinical oncology practice. These traditional chemotherapeutics agents act by killing all cells that divide rapidly, one of the main properties of most cancer cells. However, these agents also kill growing normal cells and thus these agents are not considered to be "targeted" approaches to killing cancer cells. IN recent years a large group of cancer therapeutic agents has been developed that target cancer cells where the therapeutic agent specifically attacks a protein that is only expressed by the cancer cells and not by normal cells. This approach is considered to be a "targeted" approach to cancer therapy. Most recently, another approach to killing cancer cells in a targeted fashion has been to specifically modulate the immune system to enhance that ability of the cancer patient's immune system to kill cancer cells.

Therapeutic agents that target the tyrosine-protein kinase receptor UFO protein, which can also be referred to as AXL, have shown promise in early clinical trials. However, only those patients whose cancer cells express high amounts of the AXL protein are likely to benefit from treatment with such AXL-targeted therapeutic agents. The methods below provide a quantitative proteomics-based assay that delivers a relevant measure of activation of the AXL signal pathway as AXL is not normally expressed in normal tissue and/or normal epithelial cells. In particular, the methods provide a mass spectrometry assay that quantifies AXL in formalin fixed tissues from cancer patients and that enables improved treatment decisions for cancer therapy.

Specific peptides derived from subsequences of the tyrosine-protein kinase receptor UFO protein, also referred to as AXL, and be referred to herein as AXL, are provided. The peptide sequence and fragmentation/transition ions for each peptide are particularly useful in a mass spectrometry-based Selected Reaction Monitoring (SRM), which can also be referred to as a Multiple Reaction Monitoring (MRM) assay, and will be referred to as SRM/MRM. The use of peptides for SRM/MRM quantitative analysis of the AXL protein is described.

This SRM/MRM assay can be used to measure relative or absolute quantitative levels of one or more of the specific peptides from the AXL protein and therefore provide a means of measuring by mass spectrometry the amount of the AXL protein in a given protein preparation obtained from a biological sample.

More specifically, the SRM/MRM assay can measure these peptides directly in complex protein lysate samples prepared from cells procured from patient tissue samples, such as formalin fixed cancer patient tissue. Methods of preparing protein samples from formalin-fixed tissue are described in U.S. Pat. No. 7,473,532, the contents of which are hereby incorporated by reference in their entirety. The methods described in U.S. Pat. No. 7,473,532 may conveniently be carried out using Liquid Tissue reagents and protocol available from Expression Pathology Inc. (Rockville, Md.).

The most widely and advantageously available form of tissues from cancer patients tissue is formalin fixed, paraffin embedded tissue. Formaldehyde/formalin fixation of surgically removed tissue is by far the most common method of preserving cancer tissue samples worldwide and is the accepted convention for standard pathology practice. Aqueous solutions of formaldehyde are referred to as formalin. "100%" formalin consists of a saturated solution of formaldehyde (about 40% by volume or 37% by mass) in water, with a small amount of stabilizer, usually methanol, to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin fixed cancer tissue will be the most accepted and heavily utilized methods for analysis of cancer patient tissue.

Results from the SRM/MRM assay can be used to correlate accurate and precise quantitative levels of the AXL protein within the specific tissue samples (e.g., cancer tissue sample) of the patient or subject from whom the tissue (biological sample) was collected and preserved. This not only provides diagnostic information about the cancer, but also permits a physician or other medical professional to determine appropriate therapy for the patient. Such an assay that provides diagnostically and therapeutically important information about levels of protein expression in a diseased tissue or other patient sample is termed a companion diagnostic assay. For example, such an assay can be designed to diagnose the stage or degree of a cancer and determine a therapeutic agent to which a patient is most likely to respond.

SUMMARY

The assays described herein measure relative or absolute levels of specific unmodified peptides from the AXL protein and also can measure absolute or relative levels of specific modified peptides from the AXL protein. Examples of modifications include phosphorylated amino acid residues and glycosylated amino acid residues that are present on the peptides.

Relative quantitative levels of the AXL protein are determined by the SRM/MRM methodology, for example by comparing SRM/MRM signature peak areas (e.g., signature peak area or integrated fragment ion intensity) of an individual AXL peptide in different samples. Alternatively, it is possible to compare multiple SRM/MRM signature peak areas for multiple AXL signature peptides, where each peptide has its own specific SRM/MRM signature peak, to determine the relative AXL protein content in one biological sample with the AXL protein content in one or more additional or different biological samples. In this way, the amount of a particular peptide, or peptides, from the AXL protein, and therefore the amount of the AXL protein, is determined relative to the same AXL peptide, or peptides, across 2 or more biological samples under the same experimental conditions. In addition, relative quantitation can be determined for a given peptide, or peptides, from the AXL protein within a single sample by comparing the signature peak area for that peptide by SRM/MRM methodology to the signature peak area for another and different peptide, or peptides, from a different protein, or proteins, within the same protein preparation from the biological sample. In this way, the amount of a particular peptide from the AXL protein, and therefore the amount of the AXL protein, is determined relative one to another within the same sample. These approaches generate quantitation of an individual peptide, or peptides, from the AXL protein to the amount of another peptide, or peptides, between samples and within samples, wherein the amounts as determined by signature peak area are relative one to another, regardless of the absolute weight to volume or weight to weight amounts of the AXL peptide in the protein preparation from the biological sample. Relative quantitative data about individual signature peak areas between different samples are normalized to the amount of protein analyzed per sample. Relative quantitation can be performed across many peptides from multiple proteins and the AXL protein simultaneously in a single sample and/or across many samples to gain insight into relative protein amounts, such as one peptide/protein with respect to other peptides/proteins.

Absolute quantitative levels of the AXL protein are determined by, for example, the SRM/MRM methodology whereby the SRM/MRM signature peak area of an individual peptide from the AXL protein in one biological sample is compared to the SRM/MRM signature peak area of a spiked internal standard. In one embodiment, the internal standard is a synthetic version of the same exact AXL peptide that contains one or more amino acid residues labeled with one or more heavy isotopes. Such isotope labeled internal standards are synthesized so that when analyzed by mass spectrometry a standard generates a predictable and consistent SRM/MRM signature peak that is different and distinct from the native AXL peptide signature peak and which can be used as a comparator peak. Thus when the internal standard is spiked into a protein preparation from a biological sample in known amounts and analyzed by mass spectrometry, the SRM/MRM signature peak area of the native peptide is compared to the SRM/MRM signature peak area of the internal standard peptide, and this numerical comparison indicates either the absolute molarity and/or absolute weight of the native peptide present in the original protein preparation from the biological sample. Absolute quantitative data for fragment peptides are displayed according to the amount of protein analyzed per sample. Absolute quantitation can be performed across many peptides, and thus proteins, simultaneously in a single sample and/or across many samples to gain insight into absolute protein amounts in individual biological samples and in entire cohorts of individual samples.

The SRM/MRM assay method can be used to aid diagnosis of the stage of cancer, for example, directly in patient-derived tissue, such as formalin fixed tissue, and to aid in determining which therapeutic agent would be most advantageous for use in treating that patient. Cancer tissue that is removed from a patient either through surgery, such as for therapeutic removal of partial or entire tumors, or through biopsy procedures conducted to determine the presence or absence of suspected disease, is analyzed to determine whether or not a specific protein, or proteins, and which forms of proteins, are present in that patient tissue. Moreover, the expression level of a protein, or multiple proteins, can be determined and compared to a "normal" or reference level found in healthy tissue. Normal or reference levels of proteins found in healthy tissue may be derived from, for example, the relevant tissues of one or more individuals that do not have cancer. Alternatively, normal or reference levels may be obtained for individuals with cancer by analysis of relevant tissues not affected by the cancer. Assays of protein levels (e.g., AXL levels) can also be used to diagnose the stage of cancer in a patient or subject diagnosed with cancer by employing the AXL levels. The level of an individual AXL peptide is defined as the molar amount of the peptide determined by the SRM/MRM assay per total amount of protein lysate analyzed. Information regarding AXL can thus be used to aid in determining the stage or grade of a cancer by correlating the level of the AXL protein (or fragment peptides of the AXL protein) with levels observed in normal tissues. Once the quantitative amount of the AXL protein has been determined in the cancer cells, that information can be matched to a list of therapeutic agents (chemical and biological) developed to specifically treat cancer tissue that is characterized by, for example, abnormal expression of the protein or protein(s) (e.g., AXL) that were assayed. Matching information from an AXL protein assay to a list of therapeutic agents that specifically targets, for example, the AXL protein or cells/tissue expressing the protein, defines what has been termed a personalized medicine approach to treating disease. The assay methods described herein form the foundation of a personalized medicine approach by using analysis of proteins from the patient's own tissue as a source for diagnostic and treatment decisions.

BRIEF DESCRIPTION OF THE DRAWINGS

FIG. 1 (A-C) shows results of an SRM/MRM assay of a single peptide from the AXL protein performed on a positive control sample (not formalin fixed) and a Liquid Tissue lysate from a formalin fixed biological sample with quantitation of the AXL peptide conducted on a triplequadrupole mass spectrometer. The specific characteristics about the precursor and transitions ions used to measure, using the SRM/MRM method, this peptide in biological samples that have been fixed in formalin are shown.

DETAILED DESCRIPTION

In principle, any predicted peptide derived from the AXL protein, prepared for example by digesting with a protease of known specificity (e.g. trypsin), can be used as a surrogate reporter to determine the abundance of AXL protein in a sample using a mass spectrometry-based SRM/MRM assay. Similarly, any predicted peptide sequence containing an amino acid residue at a site that is known to be potentially modified in the AXL protein also might potentially be used to assay the extent of modification of the AXL protein in a sample.

AXL fragment peptides may be generated by a variety of means including by the use of the Liquid Tissue protocol provided in U.S. Pat. No. 7,473,532. The Liquid Tissue protocol and reagents are capable of producing peptide samples suitable for mass spectroscopic analysis from formalin fixed paraffin embedded tissue by proteolytic digestion of the proteins in the tissue/biological sample. In the Liquid Tissue protocol the tissue/biological is heated in a buffer for an extended period of time (e.g., from about 80° C. to about 100° C. for a period of time from about 10 minutes to about 4 hours) to reverse or release protein cross-linking. The buffer employed is a neutral buffer, (e.g., a Tris-based buffer, or a buffer containing a detergent). Following heat treatment the tissue/biological sample is treated with one or more proteases, including but not limited to trypsin, chymotrypsin, pepsin, and endoproteinase Lys-C for a time sufficient to disrupt the tissue and cellular structure of said biological sample and to liquefy said sample (e.g., a period of time from 30 minutes to 24 hours at a temperature from 37° C. to 65° C.). The result of the heating and proteolysis is a liquid, soluble, dilutable biomolecule lysate.

Surprisingly, it was found that many potential peptide sequences from the AXL protein are unsuitable or ineffective for use in mass spectrometry-based SRM/MRM assays for reasons that are not immediately evident. As it was not possible to predict the most suitable peptides for MRM/SRM assay, it was necessary to experimentally identify modified and unmodified peptides in actual Liquid Tissue lysates to develop a reliable and accurate SRM/MRM assay for the AXL protein. While not wishing to be bound by any theory, it is believed that some peptides might, for example, be difficult to detect by mass spectrometry because they do not ionize well or produce fragments distinct from other proteins. Peptides may also fail to resolve well in separation (e.g., liquid chromatography), or may adhere to glass or plastic ware.

AXL peptides found in various embodiments of this disclosure (e.g., Tables 1 and 2) were derived from the AXL protein by protease digestion of all the proteins within a complex Liquid Tissue lysate prepared from cells procured from formalin fixed cancer tissue. Unless noted otherwise, in each instance the protease was trypsin. The Liquid Tissue lysate was then analyzed by mass spectrometry to determine those peptides derived from the AXL protein that are detected and analyzed by mass spectrometry. Identification of a specific preferred subset of peptides for mass-spectrometric analysis is based on; 1) experimental determination of which peptide or peptides from a protein ionize in mass spectrometry analyses of Liquid Tissue lysates, and 2) the ability of the peptide to survive the protocol and experimental conditions used in preparing a Liquid Tissue lysate. This latter property extends not only to the amino acid sequence of the peptide but also to the ability of a modified amino acid residue within a peptide to survive in modified form during the sample preparation.

Protein lysates from cells procured directly from formalin (formaldehyde) fixed tissue were prepared using the Liquid Tissue reagents and protocol that entails collecting cells into a sample tube via tissue microdissection followed by heating the cells in the Liquid Tissue buffer for an extended period of time. Once the formalin-induced cross linking has been negatively affected, the tissue/cells are then digested to completion in a predictable manner using a protease, as for example including but not limited to the protease trypsin. Each protein lysate is turned into a collection of peptides by digestion of intact polypeptides with the protease. Each Liquid Tissue lysate was analyzed (e.g., by ion trap mass spectrometry) to perform multiple global proteomic surveys of the peptides where the data was presented as identification of as many peptides as could be identified by mass spectrometry from all cellular proteins present in each protein lysate. An ion trap mass spectrometer or another form of a mass spectrometer that is capable of performing global profiling for identification of as many peptides as possible from a single complex protein/peptide lysate is typically employed. Ion trap mass spectrometers however may be the best type of mass spectrometer for conducting global profiling of peptides. Although an SRM/MRM assay can be developed and performed on any type of mass spectrometer, including a MALDI, ion trap, or triple quadrupole, the most advantageous instrument platform for an SRM/MRM assay is often considered to be a triple quadrupole instrument platform.

Once as many peptides as possible were identified in a single MS analysis of a single lysate under the conditions employed, then that list of peptides was collated and used to determine the proteins that were detected in that lysate. That process was repeated for multiple Liquid Tissue lysates, and the very large list of peptides was collated into a single dataset. That type of dataset can be considered to represent the peptides that can be detected in the type of biological sample that was analyzed (after protease digestion), and specifically in a Liquid Tissue lysate of the biological sample, and thus includes the peptides for specific proteins, such as for example the AXL protein.

In one embodiment, the AXL tryptic peptides identified as useful in the determination of absolute or relative amounts of the AXL protein include one or more, two or more, three or more, or four or more of the peptides of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10, each of which are listed in Table 1. Each of those peptides was detected by mass spectrometry in Liquid Tissue lysates prepared from formalin fixed, paraffin embedded tissue. Thus, each peptide is a candidate for use in developing a quantitative SRM/MRM assay for the AXL protein in human biological samples, including directly in formalin fixed patient tissue.

TABLE 1

| Peptide | Peptide Sequence |
| --- | --- |
| SEQ ID NO: 1 | GLTGTLR |
| SEQ ID NO: 2 | TATITVLPQQPR |
| SEQ ID NO: 3 | LGSLHPHTPYHIR |
| SEQ ID NO: 4 | APLQGTLLGYR |
| SEQ ID NO: 5 | YGEVFEPTVER |
| SEQ ID NO: 6 | TTEATLNSLGISEELK |
| SEQ ID NO: 7 | HGDLHSFLLYSR |
| SEQ ID NO: 8 | IYNGDYYR |
| SEQ ID NO: 9 | GQTPYPGVENSELYDYLR |
| SEQ ID NO: 10 | EDLENTLK |

The AXL tryptic peptides listed in Table 1 include those detected from multiple Liquid Tissue lysates of multiple different formalin fixed tissues of different human organs including lung, colon, and breast. Each of those peptides is considered useful for quantitative SRM/MRM assay of the AXL protein in formalin fixed tissue. Further data analysis of these experiments indicated no preference is observed for any specific peptides from any specific organ site. Thus, each of these peptides is believed to be suitable for conducting SRM/MRM assays of the AXL protein on a Liquid Tissue lysate from any formalin fixed tissue originating from any biological sample or from any organ site in the body.

An important consideration when conducting an SRM/MRM assay is the type of instrument that may be employed in the analysis of the peptides. Although SRM/MRM assays can be developed and performed on any type of mass spectrometer, including a MALDI, ion trap, or triple quadrupole, the most advantageous instrument platform for an SRM/MRM assay is often considered to be a triple quadrupole instrument platform. That type of a mass spectrometer may be considered to be the most suitable instrument for analyzing a single isolated target peptide within a very complex protein lysate that may consist of hundreds of thousands to millions of individual peptides from all the proteins contained within a cell.

In order to most efficiently implement an SRM/MRM assay for each peptide derived from the AXL protein it is desirable to utilize information in addition to the peptide sequence in the analysis. That additional information may be used in directing and instructing the mass spectrometer (e.g. a triple quadrupole mass spectrometer) to perform the correct and focused analysis of specific targeted peptide(s), such that the assay may be effectively performed.

The additional information about target peptides in general, and about specific AXL peptides, may include one or more of the mono isotopic mass of the peptide, its precursor charge state, the precursor m/z value, the m/z transition ions, and the ion type of each transition ion. Additional peptide information that may be used to develop an SRM/MRM assay for the AXL protein is shown by example for three (3) of the AXL peptides from the list in Table 1 and is shown in Table 2. Similar additional information described for the three (3) AXL peptides shown by example in Table 2 may be prepared, obtained, and applied to the analysis of the other peptides contained in Table 1.

TABLE 2

| SEQ ID | Peptide sequence | Mono Isotopic Mass | Precursor Charge State | Precursor m/z | Transition m/z | Ion Type |
|---|---|---|---|---|---|---|
| SEQ ID NO: 2 | TATITVLPQQPR | 1324.5435 | 2 | 662.883 | 625.341 | y5 |
| | | | 2 | 662.883 | 738.425 | y6 |
| | | | 2 | 662.883 | 837.494 | y7 |
| | | | 2 | 662.883 | 938.541 | y8 |
| SEQ ID NO: 4 | APLQGTLLGYR | 1188.3926 | 2 | 594.84 | 559.322 | y10 |
| | | | 2 | 594.84 | 779.441 | y7 |
| | | | 2 | 594.84 | 907.499 | y8 |
| | | | 2 | 594.84 | 1020.583 | y9 |
| SEQ ID NO: 5 | YGEVFEPTVER | 1325.4408 | 2 | 663.322 | 350.134 | b3 |
| | | | 2 | 663.322 | 601.33 | y5 |
| | | | 2 | 663.322 | 730.372 | y6 |
| | | | 2 | 663.322 | 877.441 | y7 |

The method described below was used to: 1) identify candidate peptides from the AXL protein that can be used for a mass spectrometry-based SRM/MRM assay for the AXL protein, 2) develop an individual SRM/MRM assay, or assays, for target peptides from the AXL protein in order to correlate and 3) apply quantitative assays to cancer diagnosis and/or choice of optimal therapy.

Assay Method

1. Identification of SRM/MRM candidate fragment peptides for the AXL protein
   a. Prepare a Liquid Tissue protein lysate from a formalin fixed biological sample using a protease or proteases, (that may or may not include trypsin), to digest proteins
   b. Analyze all protein fragments in the Liquid Tissue lysate on an ion trap tandem mass spectrometer and identify all fragment peptides from the AXL protein, where individual fragment peptides do not contain any peptide modifications such as phosphorylations or glycosylations
   c. Analyze all protein fragments in the Liquid Tissue lysate on an ion trap tandem mass spectrometer and identify all fragment peptides from the AXL protein that carry peptide modifications such as for example phosphorylated or glycosylated residues
   d. All peptides generated by a specific digestion method from the entire, full length AXL protein potentially can be measured, but preferred peptides used for development of the SRM/MRM assay are those that are identified by mass spectrometry directly in a complex Liquid Tissue protein lysate prepared from a formalin fixed biological sample
   e. Peptides that are specifically modified (phosphorylated, glycosylated, etc.) in patient tissue and which ionize, and thus detected, in a mass spectrometer when analyzing a Liquid Tissue lysate from a formalin fixed biological sample are identified as candidate peptides for assaying peptide modifications of the AXL protein 2. Mass Spectrometry Assay for Fragment Peptides from the AXL Protein
   a. SRM/MRM assay on a triple quadrupole mass spectrometer for individual fragment peptides identified in a Liquid Tissue lysate is applied to peptides from the AXL protein
      i. Determine optimal retention time for a fragment peptide for optimal chromatography conditions including but not limited to gel electrophoresis, liquid chromatography, capillary electrophoresis, nano-reversed phase liquid chromatography, high performance liquid chromatography, or reverse phase high performance liquid chromatography
      ii. Determine the mono isotopic mass of the peptide, the precursor charge state for each peptide, the precursor m/z value for each peptide, the m/z transition ions for each peptide, and the ion type of each transition ion for each fragment peptide in order to develop an SRM/MRM assay for each peptide.
      iii. SRM/MRM assay can then be conducted using the information from (i) and (ii) on a triple quadrupole mass spectrometer where each peptide has a characteristic and unique SRM/MRM signature peak that precisely defines the unique SRM/MRM assay as performed on a triple quadrupole mass spectrometer
   b. Perform SRM/MRM analysis so that the amount of the fragment peptide of the AXL protein that is detected, as a function of the unique SRM/MRM signature peak area from an SRM/MRM mass spectrometry analysis, can indicate both the relative and absolute amount of the protein in a particular protein lysate.
      i. Relative quantitation may be achieved by:
         1. Determining increased or decreased presence of the AXL protein by comparing the SRM/MRM signature peak area from a given AXL peptide detected in a Liquid Tissue lysate from one formalin fixed biological sample to the same SRM/MRM signature peak area of the same AXL fragment peptide in at least a second, third, fourth or more Liquid Tissue lysates from least a second, third, fourth or more formalin fixed biological samples 2. Determining increased or decreased presence of the AXL protein by comparing the SRM/MRM signature peak area from a given AXL peptide detected in a Liquid Tissue lysate from one formalin fixed biological sample to SRM/MRM signature peak areas developed from fragment peptides from other proteins, in other samples derived from different and separate biological sources, where the SRM/MRM signature peak area comparison between the 2 samples for a peptide fragment are normalized to amount of protein analyzed in each sample.
3. Determining increased or decreased presence of the AXL protein by comparing the SRM/MRM signature peak area for a given AXL peptide to the SRM/MRM signature peak areas from other fragment peptides derived from different proteins within the same Liquid Tissue lysate from the formalin fixed biological sample in order to normalize changing levels of AXL protein to levels of other proteins that do not change their levels of expression under various cellular conditions.
4. These assays can be applied to both unmodified fragment peptides and for modified fragment peptides of the AXL protein, where the modifications include but are not limited to phosphorylation and/or glycosylation, and where the relative levels of modified peptides are determined in the same manner as determining relative amounts of unmodified peptides.
ii. Absolute quantitation of a given peptide may be achieved by comparing the SRM/MRM signature peak area for a given fragment peptide from the AXL protein in an individual biological sample to the SRM/MRM signature peak area of an internal fragment peptide standard spiked into the protein lysate from the biological sample
1. The internal standard is a labeled synthetic version of the fragment peptide from the AXL protein that is being interrogated. This standard is spiked into a sample in known amounts, and the SRM/MRM signature peak area can be determined for both the internal fragment peptide standard and the native fragment peptide in the biological sample separately, followed by comparison of both peak areas
2. This can be applied to unmodified fragment peptides and modified fragment peptides, where the modifications include but are not limited to phosphorylation and/or glycosylation, and where the absolute levels of modified peptides can be determined in the same manner as determining absolute levels of unmodified peptides.
3. Apply Fragment Peptide Quantitation to Cancer Diagnosis and Treatment
a. Perform relative and/or absolute quantitation of fragment peptide levels of the AXL protein and demonstrate that the previously-determined association, as well understood in the field of cancer, of AXL protein expression to the stage/grade/status of cancer in patient tumor tissue is confirmed
b. Perform relative and/or absolute quantitation of fragment peptide levels of the AXL protein and demonstrate correlation with clinical outcomes from different treatment strategies, wherein this correlation has already been demonstrated in the field or can be demonstrated in the future through correlation studies across cohorts of patients and tissue from those patients. Once either previously established correlations or correlations derived in the future are confirmed by this assay then the assay method can be used to determine optimal treatment strategy Specific and unique characteristics about specific AXL peptides were developed by analysis of all AXL peptides on both an ion trap and triple quadrupole mass spectrometers. That information includes the monoisotopic mass of the peptide, its precursor charge state, the precursor m/z value, the transition m/z values of the precursor, and the ion types of each of the identified transitions. That information must be determined experimentally for each and every candidate SRM/MRM peptide directly in Liquid Tissue lysates from formalin fixed samples/tissue; because, interestingly, not all peptides from the AXL protein can be detected in such lysates using SRM/MRM as described herein, indicating that AXL peptides not detected cannot be considered candidate peptides for developing an SRM/MRM assay for use in quantitating peptides/proteins directly in Liquid Tissue lysates from formalin fixed samples/tissue.

A particular SRM/MRM assay for a specific AXL peptide is performed on a triple quadrupole mass spectrometer. An experimental sample analyzed by a particular AXL SRM/MRM assay is for example a Liquid Tissue protein lysate prepared from a tissue that had been formalin fixed and paraffin embedded. Data from such as assay indicates the presence of the unique SRM/MRM signature peak for this AXL peptide in the formalin fixed sample.

Specific transition ion characteristics for this peptide are used to quantitatively measure a particular AXL peptide in formalin fixed biological samples. These data indicate absolute amounts of this AXL peptide as a function of molar amount of the peptide per microgram of protein lysate analyzed. Assessment of AXL protein levels in tissues based on analysis of formalin fixed patient-derived tissue can provide diagnostic, prognostic, and therapeutically-relevant information about each particular patient. In one embodiment, this disclosure describes a method for measuring the level of the tyrosine-protein kinase receptor UFO protein (AXL) in a biological sample, comprising detecting and/or quantifying the amount of one or more modified or unmodified AXL fragment peptides in a protein digest prepared from said biological sample using mass spectrometry; and calculating the level of modified or unmodified AXL protein in said sample; and wherein said level is a relative level or an absolute level. In a related embodiment, quantifying one or more AXL fragment peptides comprises determining the amount of the each of the AXL fragment peptides in a biological sample by comparison to an added internal standard peptide of known amount, wherein each of the AXL fragment peptides in the biological sample is compared to an internal standard peptide having the same amino acid sequence. In some embodiments the internal standard is an isotopically labeled internal standard peptide comprises one or more heavy stable isotopes selected from $^{18}O$, $^{17}O$, $^{34}S$, $^{15}N$, $^{13}C$, $^{2}H$ or combinations thereof.

The method for measuring the level of the AXL protein in a biological sample described herein (or fragment peptides as surrogates thereof) may be used as a diagnostic indicator of cancer in a patient or subject. In one embodiment, the results from measurements of the level of the AXL protein may be employed to determine the diagnostic stage/grade/status of a cancer by correlating (e.g., comparing) the level of AXL protein found in a tissue with the level of that protein found in normal and/or cancerous or precancerous tissues.

Because both nucleic acids and protein can be analyzed from the same Liquid Tissue™ biomolecular preparation it is possible to generate additional information about disease diagnosis and drug treatment decisions from the nucleic acids in same sample upon which proteins were analyzed. For example, if the AXL protein is expressed by certain cells at increased levels, when assayed by SRM the data can provide information about the state of the cells and their potential for uncontrolled growth, potential drug resistance and the development of cancers can be obtained. At the same time, information about the status of the AXL genes and/or the nucleic acids and proteins they encode (e.g., mRNA molecules and their expression levels or splice variations) can be obtained from nucleic acids present in the same Liquid Tissue™ biomolecular preparation can be assessed simultaneously to the SRM analysis of the AXL protein. Any gene and/or nucleic acid not from the AXL and which is present in the same biomolecular preparation can be assessed simultaneously to the SRM analysis of the AXL protein. In one embodiment, information about the AXL protein and/or one, two, three, four or more additional proteins may be assessed by examining the nucleic acids encoding those proteins. Those nucleic acids can be examined, for example, by one or more, two or more, or three or more of: sequencing methods, polymerase chain reaction methods, restriction fragment polymorphism analysis, identification of deletions, insertions, and/or determinations of the presence of mutations, including but not limited to, single base pair polymorphisms, transitions, transversions, or combinations thereof.

The invention claimed is:

1. A method for measuring the level of the tyrosine-protein kinase receptor UFO protein (AXL) in a human biological sample of formalin-fixed tissue, comprising detecting and quantifying the amount of AXL fragment peptide in a protein digest prepared from said biological sample using mass spectrometry; and calculating the level of AXL protein in said sample, wherein said peptide is the peptide of SEQ ID NO:4; and
wherein said level is a relative level or an absolute level.

2. The method of claim 1, further comprising the step of fractionating said protein digest prior to detecting and quantifying the amount of said AXL fragment peptide.

3. The method of claim 2, wherein said fractionating step is selected from the group consisting of liquid chromatography, nano-reversed phase liquid chromatography, high performance liquid chromatography, or reverse phase high performance liquid chromatography.

4. The method of claim 1, wherein said protein digest comprises a protease digest.

5. The method of claim 4, wherein said protein digest comprises a trypsin digest.

6. The method of claim 1, wherein the mode of mass spectrometry used is Selected Reaction Monitoring (SRM), Multiple Reaction Monitoring (MRM), and/or multiple Selected Reaction Monitoring (mSRM).

7. The method of claim 1 wherein the tissue is paraffin embedded tissue.

8. The method of claim 1, wherein the tissue is obtained from a tumor.

9. The method of claim 1, wherein quantifying the AXL fragment peptide comprises comparing an amount of said AXL fragment peptide in one biological sample to the amount of the same AXL fragment peptide in a different and separate biological sample.

10. The method of claim 1, wherein quantifying said AXL fragment peptide comprises determining the amount of said AXL fragment peptide in a biological sample by comparison to an added internal standard peptide of known amount, wherein said AXL fragment said in the biological sample is compared to an internal standard peptide having the same amino acid sequence.

11. The method of claim 10, wherein the internal standard peptide is an isotopically labeled peptide.

12. The method of claim 11, wherein the isotopically labeled internal standard peptide comprises one or more heavy stable isotopes selected from $^{18}O$, $^{17}O$, $^{34}S$, $^{15}N$, $^{13}C$, $^{2}H$ or combinations thereof.

13. The method of claim 1, wherein detecting and quantifying the amount of said AXL fragment peptide in the protein digest indicates the presence of AXL protein and an association with cancer in the subject.

14. The method of claim 13, further comprising correlating the results of said detecting and quantifying the amount of said AXL fragment peptide, or the level of said AXL protein to the diagnostic stage/grade/status of the cancer.

15. The method of claim 14, wherein correlating the results of said detecting and quantifying the amount of said AXL fragment peptide, or the level of said AXL protein to the diagnostic stage/grade/status of the cancer is combined with detecting and/or quantifying the amount of other proteins or peptides from other proteins in a multiplex format to provide additional information about the diagnostic stage/grade/status of the cancer.

16. The method of claim 1, further comprising selecting for the subject from which said biological sample was obtained a treatment based on the presence, absence, or amount of said AXL fragment peptide or the level of AXL protein.

17. The method of claim 1, further comprising administering to the patient from which said biological sample was obtained a therapeutically effective amount of a therapeutic agent, wherein the therapeutic agent and/or amount of the therapeutic agent administered is based upon the amount of said AXL fragment peptide or the level of AXL protein.

18. The method of claim 17, wherein said therapeutic agent binds the AXL protein and/or inhibits its biological activity.

19. The method of claim 18, wherein the therapeutic agent is selected to specifically target AXL-expressing cancer cells.

* * * * *

```
                         SEQUENCE LISTING

<160> NUMBER OF SEQ ID NOS: 10

<210> SEQ ID NO 1
<211> LENGTH: 7
<212> TYPE: PRT
<213> ORGANISM: Homo sapiens

<400> SEQUENCE: 1

Gly Leu Thr Gly Thr Leu Arg
1               5

<210> SEQ ID NO 2
<211> LENGTH: 12
<212> TYPE: PRT
<213> ORGANISM: Homo sapiens

<400> SEQUENCE: 2

Thr Ala Thr Ile Thr Val Leu Pro Gln Gln Pro Arg
1               5                   10

<210> SEQ ID NO 3
<211> LENGTH: 13
<212> TYPE: PRT
<213> ORGANISM: Homo sapiens

<400> SEQUENCE: 3

Leu Gly Ser Leu His Pro His Thr Pro Tyr His Ile Arg
1               5                   10

<210> SEQ ID NO 4
<211> LENGTH: 11
<212> TYPE: PRT
<213> ORGANISM: Homo sapiens

<400> SEQUENCE: 4

Ala Pro Leu Gln Gly Thr Leu Leu Gly Tyr Arg
1               5                   10

<210> SEQ ID NO 5
<211> LENGTH: 11
<212> TYPE: PRT
<213> ORGANISM: Homo sapiens

<400> SEQUENCE: 5

Tyr Gly Glu Val Phe Glu Pro Thr Val Glu Arg
1               5                   10

<210> SEQ ID NO 6
<211> LENGTH: 16
<212> TYPE: PRT
```

```
<213> ORGANISM: Homo sapiens

<400> SEQUENCE: 6

Thr Thr Glu Ala Thr Leu Asn Ser Leu Gly Ile Ser Glu Glu Leu Lys
1               5                   10                  15

<210> SEQ ID NO 7
<211> LENGTH: 12
<212> TYPE: PRT
<213> ORGANISM: Homo sapiens

<400> SEQUENCE: 7

His Gly Asp Leu His Ser Phe Leu Leu Tyr Ser Arg
1               5                   10

<210> SEQ ID NO 8
<211> LENGTH: 8
<212> TYPE: PRT
<213> ORGANISM: Homo sapiens

<400> SEQUENCE: 8

Ile Tyr Asn Gly Asp Tyr Tyr Arg
1               5

<210> SEQ ID NO 9
<211> LENGTH: 18
<212> TYPE: PRT
<213> ORGANISM: Homo sapiens

<400> SEQUENCE: 9

Gly Gln Thr Pro Tyr Pro Gly Val Glu Asn Ser Glu Leu Tyr Asp Tyr
1               5                   10                  15

Leu Arg

<210> SEQ ID NO 10
<211> LENGTH: 8
<212> TYPE: PRT
<213> ORGANISM: Homo sapiens

<400> SEQUENCE: 10

Glu Asp Leu Glu Asn Thr Leu Lys
1               5
```